United States Patent [19]

Cirignano

[11] Patent Number: 4,989,464
[45] Date of Patent: Feb. 5, 1991

[54] METHOD AND APPARATUS FOR DETERMINING PARTICLE SIZE DISTRIBUTION

[75] Inventor: Paul C. Cirignano, Braintree, Mass.

[73] Assignee: W. R. Grace & Co.-Conn., New York, N.Y.

[21] Appl. No.: 520,331

[22] Filed: May 7, 1990

Related U.S. Application Data

[62] Division of Ser. No. 384,942, Jul. 25, 1989, Pat. No. 4,957,010.

[51] Int. Cl.$^5$ .......................................... G01N 15/02
[52] U.S. Cl. ..................................... 73/865.5; 366/100
[58] Field of Search ............... 73/865.5; 209/237, 239, 209/281-283, 352; 366/101, 106, 107

[56] References Cited

U.S. PATENT DOCUMENTS

| | | | |
|---|---|---|---|
| 1,530,193 | 3/1925 | Montgomery. | |
| 2,611,486 | 9/1952 | Varcoe | 209/237 |
| 3,161,587 | 12/1964 | Bach | 209/3 |
| 3,620,368 | 11/1971 | Comis et al. | 209/2 |
| 3,627,211 | 12/1971 | Leach | 241/3 |
| 3,686,068 | 8/1972 | Leach | 161/168 |
| 3,719,276 | 3/1973 | Allen et al. | 209/240 |
| 3,864,602 | 2/1975 | Feder | 317/2 |
| 4,207,378 | 6/1980 | Klein | 428/402 |
| 4,249,655 | 2/1981 | Paturess et al. | 209/31 |
| 4,261,817 | 4/1981 | Edwards et al. | 209/321 |
| 4,427,157 | 1/1984 | Klein | 241/15 |
| 4,781,983 | 11/1988 | Stickley | 428/407 |

OTHER PUBLICATIONS

Ward, "Oscillating Air Column Method for the Dry Separation of Fine and Subsieve Particle Sizes", Powder Technology, 24, No. 2, Nov.-Dec., 1979, pp. 151-154.

Allen-Bradley Sonic Sifter Brochure, Allen-Bradley Co., Milwaukee, Wis., Aug., 1965.

*Primary Examiner*—Robert Raevis
*Attorney, Agent, or Firm*—Kevin S. Lemack; William L. Baker

[57] ABSTRACT

A method and apparatus for determining particle size distribution of lightweight material such as shredded expanded polystyrene. An agitator cap assembly initially contains the material and agitates it to avoid clogging, etc. A plurality of sieves are stacked on a receptacle, and the material is driven from the agitator caps through the sieves. The amount of material retained on and passed through the sieves provides a measure of the particle size distribution.

7 Claims, 4 Drawing Sheets

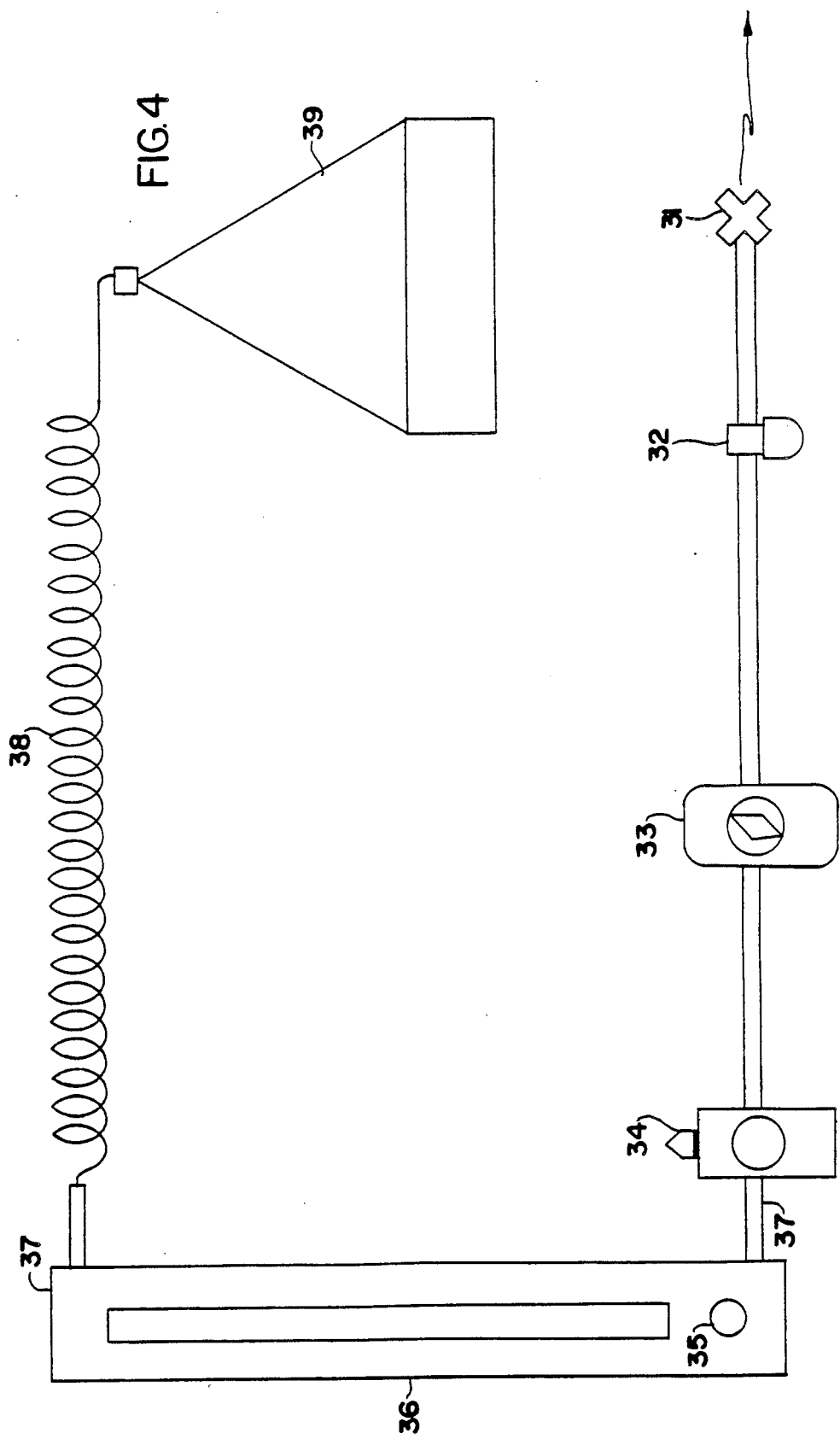

METHOD AND APPARATUS FOR DETERMINING PARTICLE SIZE DISTRIBUTION

This is a division of application Ser. No. 07/384,942, filed Jul. 25, 1989, now U.S. Pat. No. 4,957,010.

BACKGROUND OF THE INVENTION

The present invention is directed towards a method and apparatus for determining the particle size distribution of materials in general, and in particular, a method and apparatus for determining the particle size distribution of lightweight expanded polymers, such as shredded expanded polystyrene.

In the course of erecting steel structures, a thick coating of inorganic material is commonly applied to the metallic structural elements to achieve a number of objectives including fire retardance, improved appearance and sound deadening. While several types of formulations have been applied for these purposes over the years by means of a variety of techniques, a successful system consists in spraying onto the steel surface settable aqueous mixes composed essentially of calcined gypsum, a lightweight inorganic aggregate material such as exfoliated vermiculite, a mixture of fibrous materials such as a high wet bulking cellulose fiber and glass fiber, and an air entraining agent. A composition of this type is described by Bragg in U.S. Pat. Nos. 3,719,573 and 3,839,059, along with the most desirable application technique, i.e., pumping the aqueous mix and spraying it directly onto the steel in one layer.

However, vermiculite is a naturally occurring mineral which is subject to variation in quality, consistency, and uniformity. Moreover, since the vermiculite mineral must be expanded at very high temperatures prior to use, its costs is subject to unpredictable variation in energy cost.

An alternative to the gypsum-vermiculite mixes is disclosed in co-pending U.S. patent application Ser. No. 384,941, assigned to the assignee of the instant invention. Specifically, sprayable cementitious compositions containing shredded polystyrene having particular particle size distribution limits as a lightweight aggregate are taught as fireproofing compositions for structural steel members. Uniform consistency and quality of the compositions, defined in terms of pumpability, hangability and yield, are achieved by controlling the size distribution of the shredded expanded polystyrene in the product.

Apparatus for and methods of sieving and determining particle sizes of various substances are known. For example, U.S. Pat. No. 4,261,817 discloses sieving apparatus for use in determining the fineness of granular substances. The apparatus includes a suction chamber connected to a sieve by a plurality of chambers. A partial vacuum is applied to the chamber which pulls fine particles within the sieve through the sieve cloth into the suction chamber. Radial air inlet passages allow air to flow into the sieve case to agitate the sample.

U.S. Pat. No. 2,611,486 discloses apparatus for use in classifying granular material according to particle size. A vortex is formed in a chamber to disturb particles upon a sieve in the chamber in such a manner as to allow the small size particles to pass through the sieve.

However, heretofore no suitable method or apparatus existed for determining the particle size distribution of lightweight expanded polymers such as shredded expanded polystyrene. For example, the foregoing prior art does not address difficulties encountered in attempting to determine particle size distribution of lightweight expanded polymers, such as minimization of moisture, prevention of clogging of the apparatus, and minimization of static charge. Accordingly, the instant invention is directed towards a method and apparatus for determining the particle size distribution of such materials.

SUMMARY OF THE INVENTION

In accordance with one aspect of the present invention, an apparatus is provided for use in classifying the particle size distribution of a lightweight material such as shredded expanded polystyrene. The apparatus includes filtering or size segregating means such as a plurality of sieves, supported on a receptacle, and an agitator cap assembly for initially containing the material and into which a gas is driven to direct particles of appropriate size through the filering or size segregating means. Means is provided for connecting the agitator cap assembly to a gas supply.

According to another aspect of the present invention, there is provided a method of determining the particle size distribution of a lightweight material, including the steps of introducing the material to an agitator cap assembly, directing the material through filtering or size segregating means such as a series of sieves, and measuring the amount of material retained on and/or passed through said means. Where the nature of the material requires, the method also includes the step of applying an anti-static agent to the material.

BRIEF DESCRIPTION OF THE DRAWINGS

FIG. 4 is a diagrammatic view of the gas supply line used in connection with the apparatus of the present invention.

DETAILED DESCRIPTION OF THE INVENTION

Figure 1:
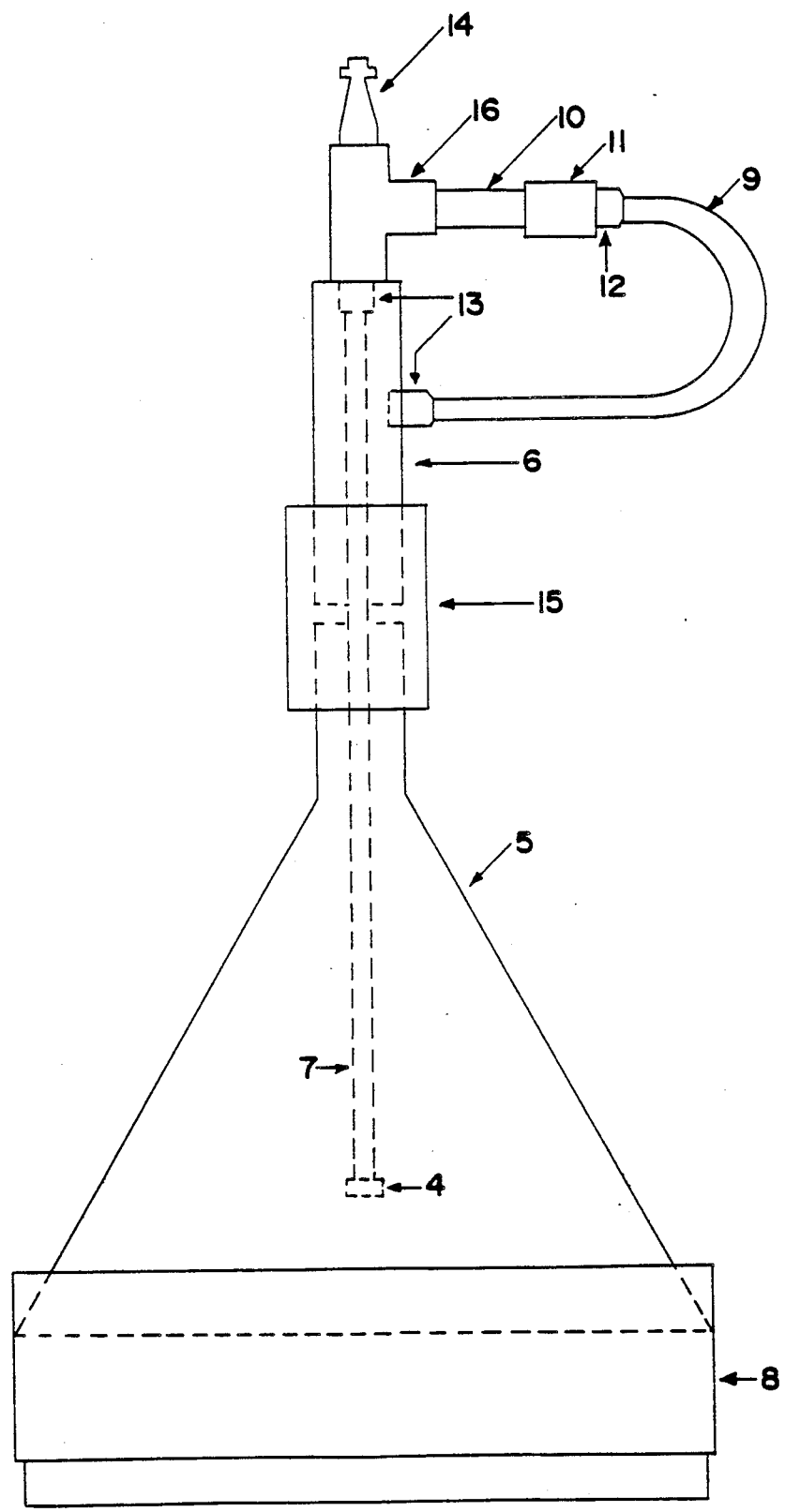
FIG. 1 is a front view of an agitator cap assembly forming part of the apparatus of the present invention.

Turning now to FIG. 1, there is shown an agitator cap assembly which forms part of the apparatus used for measuring the particle size distribution of a given sample of lightweight expanded polymer. The assembly includes a conical portion 5 such as an inverted 8" Nalgene funnel. The funnel communicates with gas supply means via tubing 6, such as ¾" PVC pipe, attached to the funnel with coupling 15. A gas such as air is driven from the gas supply means through a quick disconnect mechanism 14, a ⅛" NPT (normal pipe thread) tee 16, and tubing 6 into the chamber means to create a downward draft. The mechanism 14 comprises a male fitting coupled to the tee 16 and a female fitting for connection to the gas supply line (not shown). The mechanism 14 allows for easy and quick connection/disconnection between the agitator cap assembly and the air supply, without the use of tools and without turning off the gas pressure. The assembly also includes means to agitate the sample, such as the gas emitted from a flexible gas driven tube 7 which causes it to randomly move in the conical portion 5 so as to create gas turbulence which prevents the sample from packing onto the screen of sieve 8. The tube 7, preferably formed of latex rubber, should be positioned about three inches above the screen to optimize the agitation of the sample. A weight 4 of about 6.6 grams can be attached to tube 7 to achieve superior agitation.

The downward draft forces paticles loosened by the agitation tube 7 through the screen of sieve 8. The gas supply for the downward draft can be tapped off the main supply (which also communicates with tube 7) via a bypass loop 9, which also can be latex tubing. Incorporated in this loop is means to automatically regulate the correct gas pressure and flow rate through the bypass loop, such as a specially designed ⅛ inch close nipple 10 having an inside diameter of 3/32 inches. The nipple is made from a ⅛ inch by ¾ inch NPT close nipple by thoroughly cleaning and degreasing the nipple in a solvent such as acetone. The nipple is then filled with epoxy. When cured, a 3/32 inch diameter hole is drilled in the center of the epoxy, and carefully cleaned out to remove any loose particles without enlarging the hole. The nipple 10 is connected to bypass loop 9 via coupling means 11 and connector means 12. A similar connector means 13 connects the loop 9 to the piping 6.

Gas pressure, flow rate and duration time are critical factors that must be controlled for the apparatus to function optimally. The gas supply pressure and flow rate must be set so as to create a sufficient downward draft to force appropriate particles that can pass through the filtering or size segregating means, such as sieves, to do so as well as to provide sufficient pressure to the tubing 7 to cause it to randomly move to create enough turbulence in the conical portion 5 to prevent the sample from packing onto the filtering or size segregating means. Air pressure of about 50–51 psi and a flow rate of about 4.9–5.0 cfm is preferred for a 20 gram sample of shredded expanded polysyrene. A time duration of at least about four minutes is preferred for each sieve to provide an accurate, reproducible representation of the particle size distribution of the 20 g sample. A 20 g sample has been found to be representative of a 360 lb. billet.

FIG. 4 shows the various elements that can be used in conjunction with the agitator cap assembly to achieve the correct parameters. A valve 31 of any suitable well known type is shown for quick start or termination of pressure to the system. A filter 32 is downstream from valve 31, and removes contaminates such as oil leaked from the gas supply source such as an air compressor (not shown). Such contaminates may have a deleterious effect on other elements in the system, as well a on the separation results. Filter 32 also helps in removing moisture from condensation from the system. If too much moisture is present for the filter 32 to handle, an air dryer (not shown) can be used. A solenoid valve and timer 33 serves to automate the duration of the particular run. Pressure regulator 34 regulates the gas supply pressure to the desired level, and is equipped with a pressure gauge capable of withstanding the desired operating pressure. A stainless steel needle valve 35 to vary the gas flow rate is built into flowmeter 36. The flowmeter 36 is connected to the line by ¼ inch NPT fittings as its entrance and exit. A ¼ inch nylon coil hose 38 is connected to the agitator cap 39, and allows for freer movement of agitator cap 39.

Figure 2:
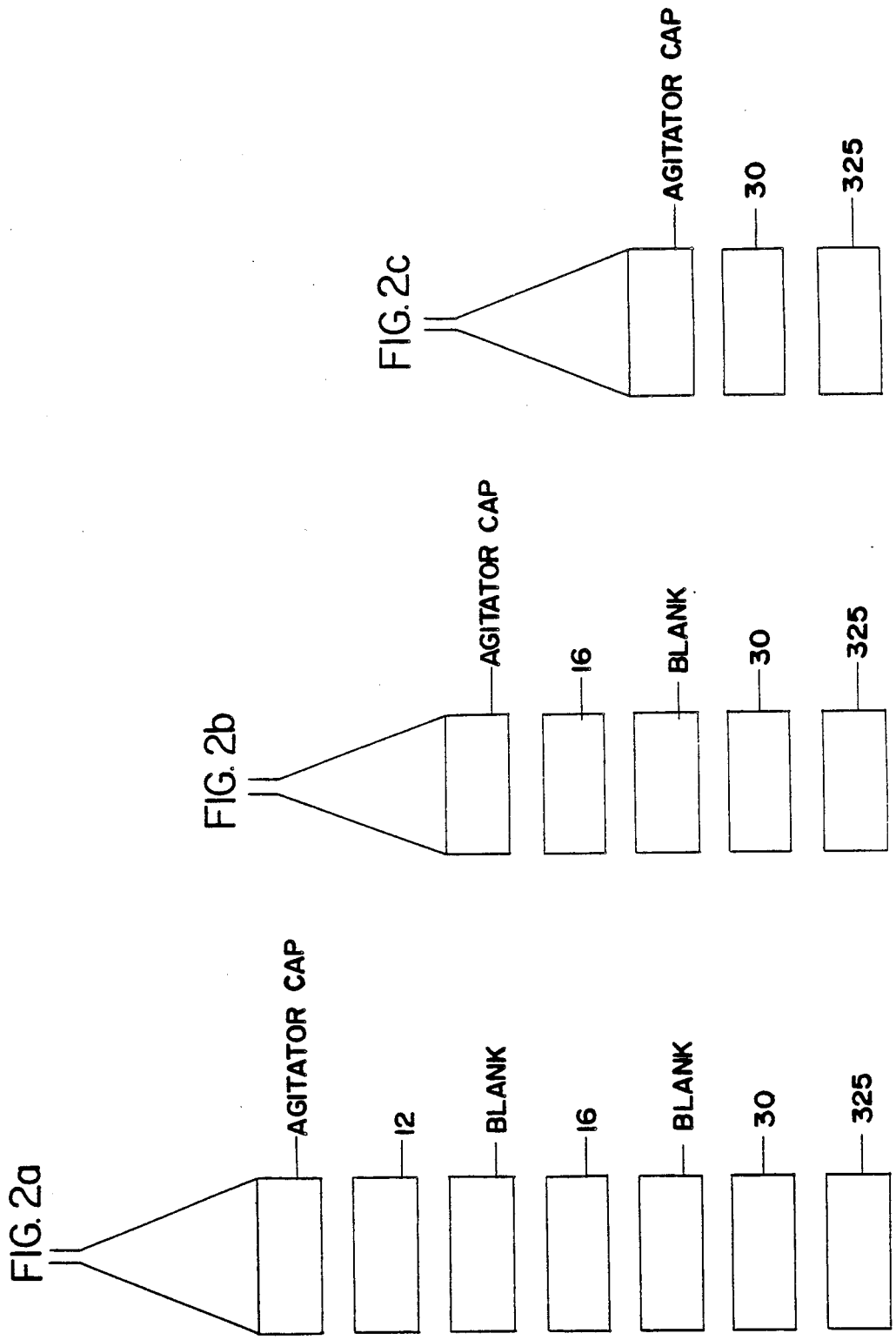
FIGS. 2a, 2b and 2c are schematics of the apparatus of the present invention.
Figure 3:
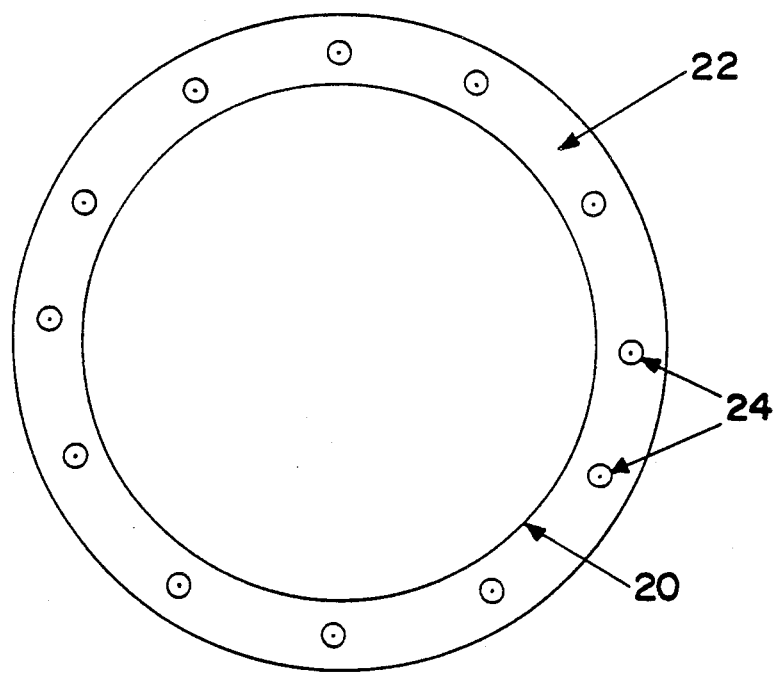
FIG. 3 is a top view of a receptacle forming a portion of the apparatus of the present invention.

The preferred procedure for determining the particle size distribution of a given sample is as follows. The agitator cap assembly is connected to air supply means (devoid of moisture) set at a pressure of 50–51 psi and a flow rate of 4.9–5.0 scfm. As shown in FIG. 2a, the assembly is placed in communication with a tared #12 sieve. Under the #12 sieve is placed a blank (a sieve with the screen removed) to accommodate the volume of sample used. A tared #16 sieve is placed under the blank, and in turn is followed by a second blank, a tared #30 sieve, and a tared #325 sieve. Typically no blank is required between the #30 and #325 sieves, as the sample volume has been sufficiently reduced by retention on previous screens. The entire sieve pack is then placed on a suitable receptacle which can receive any particles passing through the last sieve as well as allow the flow of air therethrough. FIG. 3 shows a top view of such a receptacle having an aperture 20 through which air and particles can pass. The assembly sits on a portion of surface 22, but does not cover holes 24. Holes 24 allow air passing into the receptacle from the assembly to escape.

A suitable sample is weighed. A suitable anti-static agent, such as a solution of 80% propanol and 20% silicone, glycol, can be added to the sample to reduce the static electricity of the lightweight expanded polymer that would otherwise build as a result of the constant agitation of the polymer. It is believed that the solution forms a thin layer on the particles without causing any detrimental particle deformation. The agitator cap is removed from the sieve pack, inverted, and the conical portion 5 is filled with the sample. The #12 sieve is then removed from the sieve pack and placed over the wide mouth of the concial portion 5 of the agitator cap so as to act as a cover. The conical portion 5, the sample, and the #12 sieve are placed back on the sieve pack. Air supply is commenced at a pressure of 50–51 psi and a flow rate of 4.9–5.0 scfm, and maintained for about at least four minutes. The air supply is then ceased, the conical portion 5 removed, and the weight of the sample retained on the #12 sieve is determined. The procedure is repeated for the #16 sieve as shown in FIG. 2b, and for the #30 and #325 sieves as shown in FIG. 2c. The procedure need not be applied retained on the #325 sieve. The amount of sample passing through the #325 sieve is negligible for the present purposes. The amount of material retained on the #16 sieve is not critical.

EXAMPLE 1

20 g of expanded polystyrene shredded from a sheet having a borad density of 1.01 pcf was placed in the agitator cap in accordance with the present invention. 16 g of an anti-static solution of 80% propanol and 20% silicone/glycol was added to the sample and distributed. A tared #12 sieve was placed over the mouth of the agitator cap and the assembly was inverted and placed on a sieve stack including a blank, a tared #16 sieve, a second blank, a #30 sieve, a tared #325 sieve, and a receptacle. Air supply was commenced at a pressure of about 51 psi and a flow rate of about 4.9 scfm and maintained for four minutes. The air supply was ceased, the #12 sieve and blank were removed, and the #12 sieve was weighed. Air supply was restarted and the procedure repeated for the #16 sieve and the #30 sieve. The #16 sieve, the #30 sieve and #325 sieves were then weighed. The amount of sample retained on sieve #12, sieve #16, sieve #30 and sieve #325 based on total retained weight, is shown in Table 1.

|  | #12 Sieve | #16 Sieve | #30 Sieve | #325 Sieve |
|---|---|---|---|---|
| Wt. % Retained on Screen | 6.3 | 12.5 | 58.3 | 22.9 |

The batch from which the material was taken was used as a lightweight aggregate in a sprayable cementitious fireproofing composition. The composition exhibited excellent characteristics, including pumpability, hangability and yield.

What is claimed is:

1. A method of determining the particle size distribution of lightweight polymer material, said method comprising the steps of:
   a. introducing the material into a chamber communicating with chamber gas supply means;
   b. creating a downward draft in said chamber from said chamber gas supply means while supplying to a flexible tube disposed in said chamber gas from material agitation gas supply means so as to cause said tube to move randomly in said chamber and agitate said material, to direct said material through size segregating means in communication with said chamber; and
   c. determining the amount of material remaining on said size segregating means.

2. The method of claim 1 wherein said chamber comprises a conical portion into which gas is supplied from said chamber gas supply means to create said downward draft.

3. The method of claim 1 wherein said size segregating means comprises a plurality of sieves.

4. The method of claim 3 wherein said plurality of sieves comprises a standard #12, #16, #30 and #325 sieve.

5. The method of claim 4 wherein said step for determining the amount of material remaining on said size segregating means comprises weighing the amount of material remaining on said #12 sieve, remaining on said #16 sieve, remaining on said #30 sieve, and remaining on said #325 sieve so as to determine the total retained weight, and comparing the weight of the material remaining on said #12 sieve and said #325 sieve to said total retained weight.

6. The method of claim 1 wherein said lightweight polymer material is shredded expanded polystyrene.

7. The method of claim 6 further comprising adding to said material in said chamber an anti-static solution.

* * * * *